United States Patent
Béduer et al.

(10) Patent No.: US 10,816,823 B2
(45) Date of Patent: Oct. 27, 2020

(54) OPHTHALMIC CONTACT LENS WITH COMPRESSIBLE AFFINITY MATRIX

(71) Applicant: ECOLE POLYTECHNIQUE FEDERALE DE LAUSANNE (EPFL), Lausanne (CH)

(72) Inventors: Amélie Barbara Hildegarde Béduer, Lausanne (CH); Thomas Braschler, Chavannes-près-Renens (CH); Philippe Renaud, Préverenges (CH); François Majo, Pully (CH)

(73) Assignee: École Polytechnique Fédérale de Lausanne, Lausanne (CH)

( * ) Notice: Subject to any disclaimer, the term of this patent is extended or adjusted under 35 U.S.C. 154(b) by 437 days.

(21) Appl. No.: 15/571,276

(22) PCT Filed: May 4, 2016

(86) PCT No.: PCT/IB2016/052534
§ 371 (c)(1),
(2) Date: Nov. 2, 2017

(87) PCT Pub. No.: WO2016/178151
PCT Pub. Date: Nov. 10, 2016

(65) Prior Publication Data
US 2018/0335647 A1    Nov. 22, 2018

(30) Foreign Application Priority Data
May 4, 2015    (WO) .................. PCT/IB2015/053241

(51) Int. Cl.
G02C 7/04    (2006.01)
G02C 7/02    (2006.01)
(Continued)

(52) U.S. Cl.
CPC ............ *G02C 7/049* (2013.01); *A61F 9/0017* (2013.01); *A61K 9/0048* (2013.01);
(Continued)

(58) Field of Classification Search
CPC .......... G02C 7/049; G02C 7/04; G02C 7/022; G02C 7/047; A61K 9/00; A61K 9/0048; A61K 9/0051; A61F 9/0008; A61F 9/0017
See application file for complete search history.

(56) References Cited

U.S. PATENT DOCUMENTS 3,787,378 A    1/1974 Blank
4,484,922 A    11/1984 Rosenwald
(Continued)

FOREIGN PATENT DOCUMENTS

EP    0782016 A2    7/1997
EP    0794441 A2    9/1997
(Continued)

OTHER PUBLICATIONS

International Search Report of PCT/IB2016/052534 dated Aug. 4, 2016.
(Continued)

*Primary Examiner* — Jordan M Schwartz
(74) *Attorney, Agent, or Firm* — Rankin, Hill & Clark LLP

(57) ABSTRACT

The invention relates to a contact lens for use in the treatment of ocular inflammatory pathologies. The contact lens comprises a soft porous material coupled, in certain embodiments, with detoxifying agents. Said material and/or agents contact and neutralize inflammatory mediators present in the tear fluid of ocular pathologies patients. The nature and architecture of the soft porous material allows a greater contact area between the material itself and/or detoxifying (Continued)

agents with inflammatory mediators, in view of the reversible compression of the soft material that allows greater lachrymal fluid turnover and fluid exchange within the contact lens upon e.g. blinking.

12 Claims, 2 Drawing Sheets

(51) Int. Cl.
*A61K 9/00* (2006.01)
*A61F 9/00* (2006.01)

(52) U.S. Cl.
CPC ............ *A61K 9/0051* (2013.01); *G02C 7/022* (2013.01); *G02C 7/04* (2013.01)

(56) References Cited

U.S. PATENT DOCUMENTS

| | | |
|---|---|---|
| 4,668,506 A | 5/1987 | Bawa |
| 4,713,244 A | 12/1987 | Bawa et al. |
| 4,895,896 A | 1/1990 | Müller-Lierheim |
| 4,931,279 A | 6/1990 | Bawa et al. |
| 5,213,801 A | 5/1993 | Sakuma et al. |
| 5,472,703 A | 12/1995 | Vanderlaan et al. |
| 2001/0034500 A1 | 10/2001 | March |
| 2002/0192657 A1* | 12/2002 | Erwin .............. G01N 33/54366 435/6.11 |
| 2004/0181172 A1* | 9/2004 | Carney ................. A61B 5/145 600/573 |
| 2006/0018911 A1* | 1/2006 | Ault-Riche ...... A61K 39/39566 424/178.1 |
| 2010/0113901 A1 | 5/2010 | Zhang et al. |
| 2010/0297193 A1 | 11/2010 | Archambeau et al. |
| 2011/0104236 A1* | 5/2011 | Dana .................. A61K 38/1793 424/429 |
| 2013/0182214 A1* | 7/2013 | Hofmann ............... G02C 7/048 351/159.04 |
| 2015/0104492 A1* | 4/2015 | McDermott .......... A61L 29/085 424/429 |
| 2017/0328918 A1* | 11/2017 | Kim ........................ G02C 7/04 |

FOREIGN PATENT DOCUMENTS

| | | |
|---|---|---|
| EP | 0990924 A1 | 4/2000 |
| WO | WO9007545 A2 | 7/1990 |
| WO | WO2004080297 A1 | 9/2004 |
| WO | WO2009003226 A1 | 1/2009 |
| WO | WO2009089036 A2 | 7/2009 |
| WO | WO2010062858 A1 | 6/2010 |
| WO | WO2010068281 A2 | 6/2010 |
| WO | WO2012170682 A1 | 12/2012 |
| WO | WO2013126799 A1 | 8/2013 |
| WO | WO2016029139 A1 | 2/2016 |
| WO | WO 2017-114398 * | 7/2017 |

OTHER PUBLICATIONS

Written Opinion of the International Search Authority dated Aug. 4, 2016 for PCT/IB2016/052534.

* cited by examiner

OPHTHALMIC CONTACT LENS WITH COMPRESSIBLE AFFINITY MATRIX

CROSS REFERENCE TO RELATED APPLICATIONS

The present application is a United States national stage application of International patent application PCT/IB2016/052534, filed May 4, 2016, and claims priority to International patent application PCT/1132015/053241, filed on May 4, 2015.

TECHNICAL FIELD

The invention generally relates to devices for treating ophthalmic pathologies, in particular for treating inflammation of the ocular surface.

BACKGROUND ART

Ocular inflammation of the cornea and conjunctiva is one of the most frequent complaints in ophthalmological practice. Sterile chronic inflammation of the ocular surface may have a primary immunological origin, namely in allergies (prevalence 4-20%) or autoimmune disease, or a primary physical cause, such as in surgical or other trauma, dry eye disease (prevalence about 1% in the general population, much more in the elderly), and chemical or thermal burns. Patients are typically treated with a variety of topical therapeutics, ranging from artificial tears to corticosteroids, immunosuppressive, and anti-histaminics, with generally excellent results in the short term. However, it remains difficult to treat patients permanently because of the long-term side effects of local or systemic anti-inflammatory drug therapy. These adverse events include the development of steroid-induced glaucoma, opportunistic infections or unintended systemic effects. In addition, there are more severe conditions such as chemical or thermal burns, or chronic inflammation following ocular surgery, in which the response to current anti-inflammatory therapy is not sufficient to control the inflammation in the long run.

Regardless of the origin, sterile chronic inflammation tends to persist in part because of self-perpetuating elements. Chronic inflammatory conditions triggered by surgery, chemical or thermal burns, or chronic inflammation of the ocular surface, e.g. allergies, rosacea, blepharitis or dry eyes, share a common viscous cycle: a tissue lesion causes influx of inflammatory cells, which secrete factors that maintain or exacerbate tissue lesion and further attract inflammatory cells.

Indeed, in allergic and autoimmune conditions, the presence of offending antigens leads to a specific immune response against these antigens. The resulting tissue inflammation in turn attracts more immune cells, leading to more inflammation and tissue destruction. Likewise, in primary physical disruption of epithelial barriers, the entry of commensal bacterial products will trigger an inflammatory response, which in turn has the propensity to further compromise the epithelial barrier. In dry eye disease, the inflammation negatively affects tear film stability and osmolarity, causing further ocular surface damage and ultimately more inflammation.

The prior art attempts to minimize or eliminate diseases associated with extended wear of ophthalmic lenses all have a significant drawback. Although the use of broad spectrum antimicrobials may ward off undesirable bacteria, it is also likely to kill the normal biota of the tear fluid present in the eye. The elimination of "good" bacteria may in itself cause undesirable side effects resulting from the collapse of the eye's own immunodefense system. In addition, the large scale destruction of bacteria in the eye may lead to adverse reactions because of the release of toxins associated with the lysing of bacteria.

U.S. Pat. No. 5,472,703, EP 0782016 and EP0990924A1 disclose alternative procedures for reduction of bacterial load or toxins. U.S. Pat. No. 5,472,703 describes an ophthalmic lens for placement on the anterior surface of the eye. The lens has impregnated in it or it has coated on its surface an ester of a polyhydric aliphatic alcohol and a fatty acid in which the alcohol residue has at least one hydroxyl group. The ester is present in an amount which is effective to prevent or decrease the release of bacterial toxins when the lens is exposed to those toxins. The lens is particularly well-suited for a soft hydrogel contact lens, and advantageously eliminates, minimizes or prevents keratitis, an infection of the cornea of the eye which may occur during extended wear of the lens and may cause ulceration of the cornea. EP0990924A1 describes the use of adsorbed lactoferrin to inhibit bacterial growth. EP 0782016 discloses a contact lens containing absorbed desferrioxamine that is leachable into the liquid surrounding the eye.

Apart from typical administration of antimicrobial or antibiotic drugs, some prior art documents describe a different approach to treat ocular inflammatory diseases. For example, it is known to employ hydrogel contact lenses to dispense therapeutic agents to the eye as disclosed in U.S. Pat. Nos. 3,787,378, 4,668,506, 4,713,244, 4,484,922, 4,931,279 and 5,213,801.

WO 2010/068281 describes a lens for delivering an active agent to the cornea of the eye of a patient. In this document, the lens comprises a carrier material to release the agent which is encapsulated within the lens.

WO 2009/03226 describes a system for administering an agent ophthalmically bioactive including a contact lens with microparticles or microgels of a crosslinked polymer dispersed therein, said microparticles or microgels having trapped a bioactive agent capable of migration by diffusion in the lacrymal film.

An alternative approach is the delivery of antibodies neutralizing endogenous mediators of inflammation. For instance, EP 0794441 discloses a contact lens containing an absorbed antibody, such as anti-Interleukin-1, that is leachable into the liquid surrounding the eye, so to deliver sufficient antibody into the ocular liquid to substantially inhibit the activity of an antigen, e.g., interleukin-1. WO2013126799 discloses the release of a variety of mediators from silk matrices. While more specific, this approach still involves the delivery of foreign molecules to the ocular environment.

Additionally, a number of contact lens devices with attached antibodies on the lens surface have been described in the art. These solutions provide removal of inflammatory mediators without leaching a foreign molecule into the ocular environment by exploiting a capture molecule present on the contact lens.

For instance, WO2016029139 discloses a contact lens biosensor, the function of which is to analytically detect the presence of small amounts of endogenous biomarkers in tears. However, simple surface coating does not in general yield the necessary adsorption capacity which would be needed if such a device were to be used to significantly reduce ocular inflammation by removal of a pro-inflammatory molecule.

Likewise, U.S. Pat. No. 4,895,896A discloses a contact lens with covalently attached antibodies directed against constituents of the tear film such as mucines and albumin. While this allows lubrication and passivation of the contact lens, the device has to be carefully designed not to capture too much tear film constituents to guarantee tear film stability.

To enable significant turnover of tear film environment for an extended amount of time, a substantial adsorption capacity is needed. For major mediators present in substantial concentrations, this cannot be obtained by surface coated devices. Porous materials typically provide such a high surface to volume ratio. For instance, WO9007545 discloses a porous affinity matrix, designed to capture substantial amounts of biomolecules for blood purification.

Despite the available tools and means for treating pathological conditions of the eyes with an infection/inflammation component, there is still a need of identifying novel alternative treatment modalities for (chronic) inflammatory disease of the ocular surface.

SUMMARY OF INVENTION

The present invention, as described hereinafter and in the appended claims, relates to a "smart" contact lens designed to capture pro-inflammatory factors present in the tears in order to improve clinical outcome of patients suffering from chronic ocular inflammation with diverse origins. The invention aims at continuously subtracting harmful endogenous mediators from the tear fluid, rather than following the established treatment route of adding anti-inflammatory molecules. The purpose of the smart ophthalmic lens device is to bring the vicious circle of chronic inflammation to a halt by a continuous removal of involved inflammatory mediators from the tear film, thus reducing or avoiding the need for anti-inflammatory drugs.

Contrary to the usual approaches exploiting devices such as contact lens for treating ocular infections/inflammations, the instant invention presents peculiar features which permits to overcome the prior art's drawbacks in a simple and elegant manner. In fact, the "smart" ophthalmic contact lens is made of or incorporates a porous, soft material with specific features. Such a material is endowed with the capacity to take up at least one inflammatory mediator present on the ocular environment, and in particular, preferred embodiments into the tear liquid. This capacity arises either from intrinsic properties of the material (for instance, when using a porous heparin sulfate structure capable of binding histamine), or because an otherwise inert porous material is surface- or bulk-functionalized with a bioactive agent with an affinity for the inflammatory mediators. For the grafting of affinity agents to the soft porous material, numerous covalent linking technique exist. Depending on the functional groups available on the affinity agent and the soft porous material, chemical coupling based on carbodiimide, epoxy, silane, click chemistry (azide alkyne addition), Michelson addition and many more, known in the art, can be used.

These features allow contacting and neutralizing the inflammatory mediators commonly present in e.g. the tear fluid without systemically or locally releasing potentially harmful active agents in the patient's body. On the contrary, the smart contact lens acts as a sponge, absorbing such inflammatory mediators and removing them when the contact lens is removed. In fact, the porous nature of the soft porous material exponentially enhances the contact surface, thus creating at the same time a higher detoxifying active surface. The contact lens of present invention elegantly addresses the combined need for an efficient fluid flow and high surface-to-volume ratio through the soft, porous, reversibly compressible affinity matrix comprised therein, thus providing an efficient non-leachable anti-inflammatory action as well as an effective biomolecule removal.

The soft character of the porous material gives useful traits to the contact lens in terms of drainage and turn-over of the tear fluid within the therapeutically-active lens surface compared to solutions known in the art. Namely, during the blinking cycle, the varying degree of hydration of the eye can be exploited with a suitable choice of compressibility and hydraulic conductivity of the soft material to achieve substantial compression and release to enhance tear fluid turnover in the pore space of the soft porous material.

The compressibility of the porous material depends both on the mechanical properties of the material of the pore walls (namely, the Young modulus) and the geometry of pores and wells (primarily the fraction of the volume occupied by the wall material, and whether the pores are open or closed).

The hydraulic conductivity depends primarily on the pore structure, increasing with pore size and also with interconnectivity of the pores.

Advantageously, the porous material can also be an index-matching material with conventional contact lenses. With this novel approach, it will be possible to reach patients not responding to established anti-inflammatory therapy, and also to make anti-inflammatory therapy in the eye more sustainable by avoiding local and systemic secondary effects associated with the current drugs.

It is therefore an object of the present invention to provide for an ophthalmic contact lens for use in the treatment or prevention of an ophthalmic pathology with an inflammatory component, said contact lens comprising or consisting of a soft porous reversibly compressible material allowing fluidic exchanges with the tear fluid so to take up and/or neutralize at least one mediator of inflammation present in said tear fluid.

In a preferred embodiment, the fluidic exchanges are obtained via a physiologically-driven reversible compression of the soft porous material. In still a preferred embodiment, the fluidic exchanges are obtained via blinking.

In one embodiment, at least one detoxifying agent is covalently bound to the soft porous material.

In a preferred embodiment, the soft porous material has a pore size comprised between about 10 nm and about 300 μm and a thickness comprised between about 1 μm and about 5 mm.

In a preferred embodiment, the soft porous material has a Young modulus comprised between about 10 Pa to about 100 kPa, preferably between about 100 Pa to about 50 kPa.

In a preferred embodiment, the ophthalmic contact lens comprises an area adapted for the vision, wherein said area is positioned in correspondence of the optical axis of the subject's eye wearing the contact lens.

In one embodiment, the soft porous material is coupled or assembled on at least a portion of at least one contact lens surface.

In one embodiment, the at least one detoxifying agent is a protein such as a growth factor, an enzyme, a transmembrane receptor, a protein receptor, a serum protein, an adhesion molecule, a neurotransmitter, a morphogenetic protein, a matrix protein; a peptide, a polypeptide, a nucleic acid sequence (e.g., DNA or RNA), a hormone, a cytokine, a polysaccharide, an antigen, a lipid molecule, a differentiation factor, a cell as well as any functional fragment thereof or any combinations thereof.

In a particular embodiment, the protein is an antibody, a multivalent antibody, a multispecific antibody, an scFv, a bivalent or trivalent scFv, a triabody, a minibody, a nanobody, a diabody, as well as any derivative, functional fragment or combinations thereof.

In a particular embodiment, the mediator of inflammation present in the tear fluid and neutralized is an antibody or histamine.

In one embodiment, a coupled lens surface and/or contact lens comprises micro-reservoirs fluidically connected with the soft porous material.

In one embodiment, the ophthalmic pathology is selected from the list comprising disorders of eyelid, lacrimal system and orbit (e.g. Blepharochalasis, Dacryoadenitis, Epiphora, Dacryocystitis, Blepharitis); disorders of sclera, cornea, conjunctiva, iris and ciliary body (e.g. Scleritis, Episcleritis, Keratitis, Corneal ulcer/Corneal abrasion, Thygeson's superficial punctate keratopathy, Keratoconjunctivitis, Uveitis, Iritis, Pterygium, Conjunctivitis, Hyposphagma, Trachoma); disorders of choroid (e.g. Chorioretinitis, Choroiditis); Inflammatory Glaucoma; Rosacea; red eye; dry eye disease; Endophthalmitis and/or Panophthalmitis.

A further object of the present invention relies in a kit comprising the above-described ophthalmic contact lens.

Figure 2:
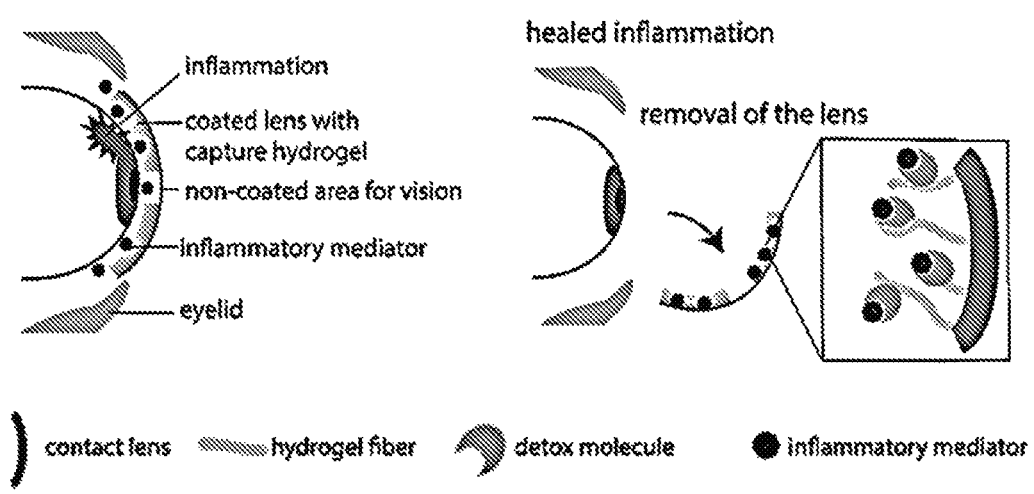
Figure 3:
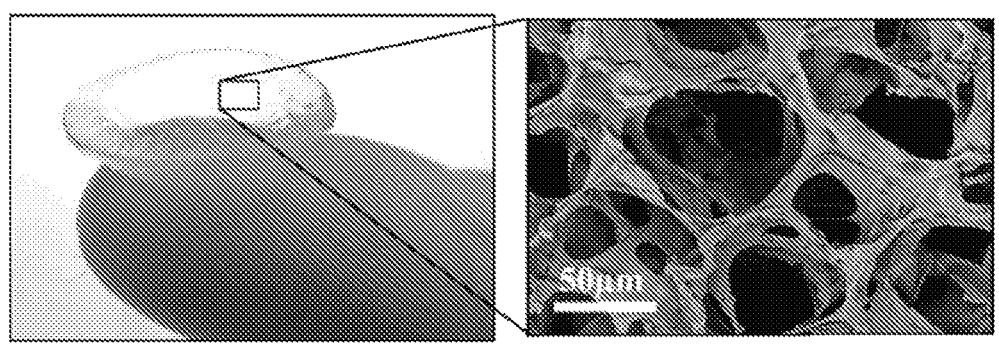

c)-d): an additional lens surface is coupled to the soft porous material and in direct contact with the eye;

e)-f): the whole lens can be constituted of a one piece of structured soft porous material;

FIG. 2 shows a sketch of the invention principle. A detoxifying contact lens with capture function is specifically designed for capturing inflammatory mediators present in the tear fluid. The inflammatory mediators diffuse through the detox porous hydrogel coated on the lens surface and functionalized with "detox molecules". At e.g. the end of the day, the patient removes the lens containing the trapped anti-inflammatory molecules. The inflammation can be healed after several days or few weeks;

FIG. 3 shows a picture of a hydrogel coated on contact lens with a microscopic view of the porous structure of the hydrogel. Pores are interconnected and fibres are flexible, allowing diffusion and deformation of the gel layer when the eye is closing.

DESCRIPTION OF EMBODIMENTS

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "and," and "the" include plural referents unless the context clearly dictates otherwise. Thus, for example, reference to "a polymeric material" includes a plurality of such polymeric materials and reference to "a detoxifying agent" includes reference to one or more detoxifying agents, and so forth.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

The contact lens of the invention comprises a soft porous materials having, once worn by a subject, a portion in direct contact with the ocular bulb surface (i.e., the conjunctiva covering the cornea and/or the sclera), and an opposite portion in contact with the inner surface of the eyelid, particularly when the eye is closed.

The soft porous material can be substantially composed of a polymeric material. As used herein, a "polymeric material" is any material comprising polymers, large molecules (also known as macromolecules) composed of many repeated smaller units, or subunits, called monomers, tightly bonded together by covalent bonds. Polymer architecture at the molecular scale can be rather diverse. A linear polymer consists of a long linear chain of monomers. A branched polymer comprises a long backbone chain with several short side-chain branches covalently attached. Cross-linked polymers have monomers of one long or short chain covalently bonded with monomers of another short or long chain. Cross-linking results in a three-dimensional molecular network; the whole polymer is a giant macromolecule. Another useful classification of polymers is based on the chemical type of the monomers: homopolymers consist of monomers of the same type, copolymers have different repeating units. Furthermore, depending on the arrangement of the types of monomers in the polymer chain, there are the following classification: the different repeating units are distributed randomly (random copolymer) or there are alternating sequences of the different monomers (alternating copolymers) in block copolymers long sequences of one monomer type are followed by long sequences of another type; and graft copolymers consist of a chain made from one type of monomer with branches of another type. Elastomers (also called rubbers) are lightly cross-linked networks while thermosets are densely cross-linked networks. Thermosets soften mildly and ultimately degrade upon heating, while thermoplastics, which do not contain crosslinks, melt upon heating and they can be reshaped repeatedly. These thermomechanical differences between polymers, owing to the significantly different organisation at the molecular scale, have important consequences both in their processing and usage. Rubbers are characterised by the property of high elasticity, i.e. elastic behaviour at high stresses and strains. Polymers can be diluted in a variety of solvents (usually organic but there are a few polymers called polyelectrolytes which are water soluble). A sufficiently dense polymer solution can be crosslinked to form a polymer gel, including a hydrogel or a cryogel, which is a soft solid.

As used herein, the term "gel" refers to a non-fluid colloidal network or polymer network that is expanded throughout its whole volume by a fluid. A gel is a solid three-dimensional network that spans the volume of a liquid medium and ensnares it through surface tension effects. The internal network structure may result from physical bonds (physical gels) or chemical bonds (chemical gels).

As used herein, the term "hydrogel" refers to a gel in which the swelling agent is water. A hydrogel is a macromolecular polymer gel constructed of a network of cross-linked polymer chains. It is synthesized from hydrophilic monomers, sometimes found as a colloidal gel in which water is the dispersion medium. Hydrogels are highly absorbent (they can contain over 90% water) natural or synthetic polymeric networks. As a result of their characteristics, hydrogels develop typical firm yet elastic mechanical properties.

Several physical properties of the (hydro)gels are dependent upon concentration. Increase in (hydro)gel concentration may change its pore radius, morphology, or its permeability to different molecular weight proteins. One skilled in the art will appreciate that the volume or dimensions (length, width, and thickness) of a (hydro)gel can be selected based on instant needs. The mechanical properties of the material can be tailored according to said needs by changing the physical or chemical properties thereof (molecular chain length, crosslinking, water content and so forth). Some examples of hydrogels include, but are not limited to, gelatin, collagen, agar, chitosan or amelogenin. A (hydro)gel may also comprise either at least one glycosaminoglycane or at least one proteoglycane, or a mixture of those two substances. The glycosaminoglycane may be for example a hyaluronic acid, chondroitinsulfate, dermatansulfate, heparansulfate, heparine, keratansulfate or combinations thereof.

Polymer materials may also be formed by blending two or more polymers into physical mixtures. For example, the rather poor impact strength of polystyrene is greatly improved by incorporating small particles of an elastomer. Many properties of polymeric materials depend on the microscopic arrangement of their molecules. Polymers can have an amorphous (disordered) or semicrystalline (partially crystalline, partially ordered) structure. Polymers can be mixed with inorganic particles (usually in the form of continuous fibres, such as glass or particulates such as mica, talc and clay) in order to modify and improve (mainly but not exclusively) their mechanical properties. Reinforcement using organic fibres (for example, kevlar (poly(paraphenylene terephthalamide) or carbon fibres) is also possible.

Further suitable polymeric materials according to the present invention may comprise one or more compounds selected from a non-exhaustive list comprising a polyaminoacid or its derivatives, preferably polylysin or gelatin, polypropylene, polypropylenoxide or their derivatives, polymethylenoxide or its derivatives, polyethylene, polyethylenoxide or their derivatives, polyacrylate or its derivatives, methyl cellulose, carboxymethyl cellulose, dextran, polysaccharides and their derivatives, preferably glycosaminoglycanes or alginate, nucleotides and their derivatives, polylipides, fatty acids and their derivatives, or any combination thereof.

Additional or alternative suitable materials for the manufacture of the porous material of the contact lens of the invention includes porous structured metal, a glass layer, a conglomerate of microparticles or combinations thereof as well as combinations with any previously disclosed material. These further materials are particularly suitable when they are shaped or otherwise conformed in thin layers so to obtain a sufficiently high surface/volume ratio (such as for instance $1/10000$ to $1/5$ ratio, advantageously comprised between $1/1000$ and $1/100$, in $m^{-1}$) to render them soft. However, these ratios are advantageous for all the used materials.

The soft porous material of the invention can be manufactured through any suitable manufacturing method known in the art allowing to create a highly interconnected net of pores in the material, such as e.g. (photo)lithography, 3D printing, inkjet printing, porogen leaching, emulsion freezing/freeze drying technique, inverse opal hydrogelation, cryogelation, electrospinning or fiber extrusion and bonding, gas foaming and so forth.

Generally speaking, the material according to the invention is at the same time both highly porous and soft. These two features represent the basis of the inventive concept behind the smart contact lens of the invention, and impart to the same peculiar mechanical as well as pharmacokinetic/pharmacodynamic attributes in terms of detoxifying action. In the frame of the present disclosure, a "soft" material is any material that is either compressible, flexible, elastic, has memory shape properties or any combination thereof. In order to be used in living subjects, moreover, the soft porous material must also imperatively be a biocompatible material suitable for ocular or non-ocular medical uses.

For its peculiarities, the soft porous material, in combination with its architecture, provides a key innovation, as it combines rapid fluid exchange kinetics with high capacity, difficult to meet with traditional surface or bulk modification. Indeed, the tear film under a conventional contact lens (<1 microliter) represents only a small fraction of the total tear volume (ca. 7 microliters), and in addition is exchanged slowly, making the surface of a standard contact lens unsuitable for rapid and high-capacity detoxification. By choosing as a material of a contact lens a porous, highly compressible and re-expandable layer, one can efficiently increase both the effective volume of the tear film under the lens and the exchange kinetics by using a physiologically-driven ocular event, such as eye blinking or any relative movement between the lens and the eyelid (as in the case of Rapid Eye Movements-REM), to trigger gel compression and therefore fluid pumping. In this context, a polymeric soft material as described above (e.g. a (hydro)gel or an elastomer) is an excellent choice.

As a consequence, it would be apparent to a skilled person that several mechanical parameters regarding the contact lens can be tailored on the sole basis of the architecture of the porous layer, including features like the thickness of the material, its porosity, the pore size and so forth. In preferred embodiments of the invention, the soft porous material has a pore size comprised between about 10 nm and 300 μm and a thickness comprised between about 1 μm and 5 mm. Concerning the pore size of the porous material, these can be advantageously tailored so to obtain a material matching the refractive index of the ocular surface, so to avoid any adverse optical effect. In this context, pores sized between 10 and 200 nm are preferred.

Figure 1:
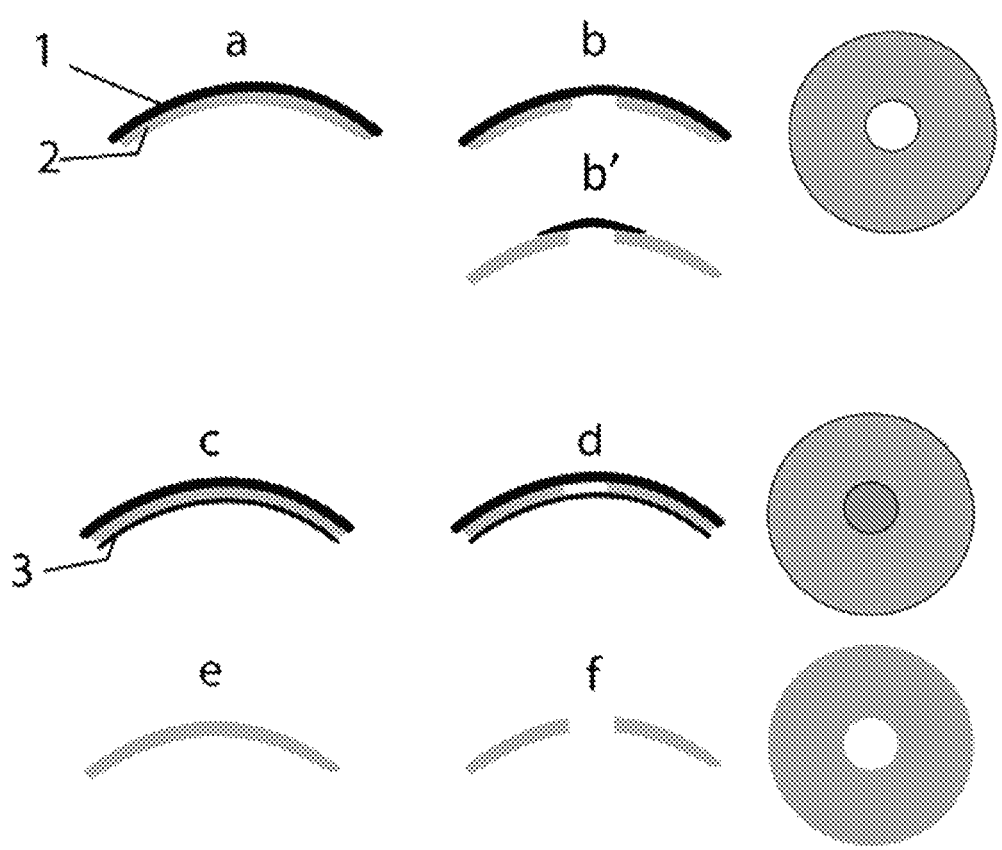
FIG. 1 shows exemplary configuration embodiments of the contact lens device. 1=coupled contact lens, 2=soft porous material, 3=coupled contact lens. a) the soft porous material is grafted to or coupled with a conventional contact lens, the material is everywhere at the surface or can be structured, for example to enable vision through the lens (central area depleted of absorbing porous material, b and b').

The soft porous material contact lens can be either molded (including using injection molding), spin-coated or 3D printed on the internal face of a "one-piece" contact lens or it can be separately manufactured through any suitable manufacturing method allowing to create pores in the material (such as e.g. (photo)lithography, 3D printing, inkjet printing, porogen leaching, emulsion freezing/freeze drying technique, inverse opal hydrogelation, cryogelation, electrospinning or fiber extrusion and bonding, gas foaming and so forth) and possibly grafted to or included within at least one additional contact lens. For example, a contact lens of the invention may be constructed by providing a first lens surface material such as a conventional contact lens and depositing a soft, porous material on it, joining them via any suitable grafting means, as shown in FIG. 1a-b-b'. Alternatively, the porous soft material can be sandwiched between two or more contact lenses surfaces in many different combinations, as for instance shown in FIG. 1c-d. The lens surface (e.g. the coupled contact lens) can be even used for correcting disorders of refraction and accommodation of the eyes as for instance Hypermetropia, Myopia, Astigmatism, Anisometropia, Presbyopia and the like through a particular geometry and/or material.

In a preferred embodiment, the soft porous material of the contact lens is a hydrogel. For example, in various embodiments, the lens material may comprise polyhydroxyethylmethacrylate (pHEMA), a silicone, or a composite comprising silicone dispersed in a hydrogel. In one embodiment, the hydrogel comprises polyhydroxyethylmethacrylate (pHEMA) or copolymers thereof. In another embodiment, the hydrogel comprises a silicone hydrogel. In still another embodiment, the hydrogel comprises hyaluronic acid. The hydrogels may be cross-linked using methods and/or materials known in the art, which are suitable for use with the ocular tissues. In one embodiment, the cross-linking agent is ethyleneglycol dimethacrylate (EGDMA).

The expression "detoxifying agent", as well as "bioactive compound" or "therapeutic agent", refers herein to an active agent, which is any agent that is biologically active, i.e. having an effect upon a living organism, tissue, or cell. The expression active agent is used herein to refer to a compound or entity that alters, inhibits, physically or chemically blocks or neutralizes, activates, or otherwise affects biological or chemical events. More particularly, a detoxifying agent is any active agent having prophylactic or therapeutic properties for what concerns ocular inflammatory events due to a pathological condition. Even more particularly, a detoxifying agent according to the present invention is a compound able to neutralize or reduce the activity of at least one mediator of inflammation present in the tear fluid. Said neutralization or reduction in activity are performed and obtained mainly by coupling, and physically interacting, with at least one inflammatory mediator present in the tear fluid. The interaction between a detoxifying agent and an inflammatory mediator physically or chemically impairs this latter so that it can no longer exert a pro-inflammatory effect.

The detoxifying agent, or agents, are coupled to the soft porous material constituting or included in the contact lens and is directed towards the eye's surface in order to interact and neutralize the inflammatory mediators present in the tear fluid. Such a coupling is preferably performed by covalently binding the detoxifying agent to the soft porous material of the by using any suitable means, such as for instance chemical immobilization via coupling through amino groups, NHS esters, aldehydes, azlactone, carbonyl diimidazole, sulfhydryl groups, maleimide, iodoacetyl groups, pyridyl disulphide groups, carbonyl ketones or aldehydes, hydrazide, carboxyl groups, carbodiimides and the like.

The detoxifying agent is preferably bond to the surface of soft porous material, but it can also be embedded within this latter. For example, it can be envisaged a scenario in which suitable polymeric materials (e.g., hydrogels) can be rapidly formed by e.g. photopolymerizing monomer solutions mixed with a detoxifying agent such as large proteins. The resulting detoxifying agent-loaded hydrogel might contain pore sizes appropriate for physical entrapment of large proteins while remaining permeable to smaller molecules, as for instance inflammatory cytokines. The open structure of these hydrogels enables even the capture of target inflammatory mediators present at low concentrations.

One skilled in the art will appreciate that a variety of therapeutic agents can be chosen depending upon the condition to be treated and/or the inflammation mediators to be targeted, which in some embodiments can be even antibodies. Exemplary therapeutic agents include, but are not limited to, a protein such as a growth factor, an enzyme, an antibody or any derivative thereof (such as e.g. multivalent antibodies, multispecific antibodies, scFvs, bivalent or trivalent scFvs, triabodies, minibodies, nanobodies, diabodies etc.), a transmembrane receptor, a protein receptor, a serum protein, an adhesion molecule, a neurotransmitter, a morphogenetic protein, a matrix protein; a peptide, a polypeptide, an antigen, a nucleic acid sequence (e.g., DNA or RNA), a hormone, a cytokine, an antigen, a polysaccharide, a lipid molecule, a differentiation factor, a cell and any functional fragment of the above, as well as any combinations thereof. A "functional fragment" is any portion of an active agent able to exert a detoxifying activity, i.e. the neutralisation or the activity reduction of at least one mediator of inflammation present in the tear fluid. For example, a functional fragment of an antibody as a detoxifying agent could be an Fc region, an Fv region, a Fab/F(ab')/F(ab')$_2$ region and so forth. As will be evident for a skilled person, the amount of the detoxifying agent(s) present in the soft porous material of the contact lens is selected to be a therapeutically effective amount. The expression "therapeutically effective amount" as used herein means that amount of a compound (e.g. a material, (macro)molecule or composition) which is effective for producing some desired therapeutic effect in a subject at a reasonable benefit/risk ratio applicable to any medical treatment. Accordingly, a therapeutically effective amount may, for example, prevent, minimize, or reverse disease progression associated with a disease or bodily condition. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amounts will depend upon a variety of factors such as the severity of the condition being treated; individual patient parameters including age, physical condition, sex, size and weight; concurrent treatments; the frequency and/or duration of treatment; general health and prior medical history of the patient being treated, and like factors well known in the medical arts. These factors are well known to those of ordinary skill in the art and can be addressed with no more than routine experimentation. In some cases, a maximum dose can be used, that is, the highest safe dose according to sound medical judgment. A physician or veterinarian having ordinary skill in the art can readily determine and prescribe the effective amount of the detoxifying agent required. For example, the physician or veterinarian could start doses of the active detoxifying agents described herein employed in the pharmaceutical composition at levels lower than that required to achieve the desired therapeutic effect and then gradually increasing the dosage until the desired effect is achieved, or vice-versa.

In certain embodiments, the contact lens device may be provided with structural features to impart a certain control over the interaction between a detoxifying agent and inflammatory mediators. For example, the contact lens device may include micro-perforations, selected areas of varying thickness and porosity, or any combination thereof, which may for example facilitate or reduce the transport of the tear fluid by altering diffusional distances or enabling fluid flow through portions of the device rather than having to rely solely on diffusional mass transport.

In certain embodiments, the soft porous material forms a substantially continuous detoxifying agent-carrying zone. This is particularly useful in cases where a pathological ocular condition involves all the ocular surface, including the surface in correspondence of the optical pathway of a subject (i.e., in correspondence of the pupil). In some embodiments, however, the substantially continuous detoxifying agent-carrying zone surrounds the optical pathway of a contact lens but does not reside in the optical pathway. In other words, in some instances the contact lens comprises an area which is adapted for the vision that does not comprise the contact lens' soft porous material, said area being positioned in correspondence of the optical axis of the subject's eye wearing the contact lens.

In one embodiment, the density and/or disposition of the detoxifying agent within the soft porous material is substantially uniform. In another embodiment, a first zone of the soft porous material have a different density and/or disposition than a second zone or further zone. For example, the soft porous material may have discrete "detoxifying regions" of higher or lower amounts of detoxifying agent disposed in/on the material. In one embodiment, a gradient may be present. In some embodiments, different zones of the soft porous material may comprise different detoxifying agents, each with a particular density and/or disposition within the polymeric soft material.

A further advantage of the detoxifying contact lens of the invention resides in its intrinsic mode of action. In fact, since the detoxifying agent(s) are physically bound (e.g. through covalent bonds) to the soft porous material, the inflammatory mediators coming into contact with the detoxifying agents can be physically removed from the inflamed milieu (i.e., the tear fluid) once the subject removes the contact lens. In such a way, in addition to the non-release of any therapeutic agent in the tear fluid, with all the associated advantages thereof, the smart device of the invention shows able to neutralize and totally eliminates those factors responsible for the inflammation.

Depending on the subject's needs, therefore, in some embodiments, the contact lens device may be worn for at least 1 hour, at least 2 hours, at least 4 hours, at least 8 hours, at least 16 hours, or even longer. In some embodiments, the device may be removed at least twice per day, at least once per day, at least once per week, or at least once per month. The device may be removed with other frequencies as well, according to the development of the pathological condition and/or the treatment schedule. After removal of the device, the same contact lens device may be re-worn (e.g., after cleaning and/or sanitizing it via for instance the dissociation of inflammatory mediators from the detoxifying agent), or a new contact lens device may be inserted.

In some embodiments, a coupled lens surface and/or contact lens can comprise micro-reservoirs in the form for instance of micro-cavities or micro-pouches fluidically connected with the soft porous material. In these microcavities, a medium as for example a liquid medicament (e.g. anesthetics, anti-inflammatory and the like) can be introduced and can come into direct contact with the cornea of a subject or otherwise released by either leaching from the contact lens via microchannels adapted so to traverse the soft porous material towards to cornea, preferably by blinking. Because of the small size of the microcavities, the liquid could be maintained within them by means of surface tension forces. In some embodiments all microcavities may have at least one channel for filling or refilling with a product, in other embodiments only one or some cavities may have at least one such channel, and possibly all the channels can converge into a single macrochannel for dispensing a medium. It is therefore possible to design different embodiments where only some selected microcavities may be (re)filled. Some microcavities may even be filled optionally, for example after the carrier has been placed on a patient depending on the evolution (to increase the concentration of a product or for any suitable subsequent purpose).

The ophthalmic contact lens of the invention is used in the treatment or prevention of a pathology with an ophthalmic inflammatory component, that is, any acute or chronic pathological condition that presents during at least one of its phases of development and/or inception an ocular inflammation stage. Many diverse pathologies are encompassed within this definition, including allergies, neoplastic diseases, physical or chemical damage of any portion of the eyes, infections, autoimmune diseases, autoinflammatory diseases, hypersensitivity and the like. In some embodiments, the ocular inflammation to be treated with the contact lens device of the invention can be selected among the list comprising disorders of eyelid, lacrimal system and orbit (e.g. Blepharochalasis, Dacryoadenitis, Epiphora, Dacryocystitis, Blepharitis); disorders of sclera, cornea, conjunctiva, iris and ciliary body (e.g. Scleritis, Episcleritis, Keratitis, Corneal ulcer/Corneal abrasion, Thygeson's superficial punctate keratopathy, Keratoconjunctivitis, Uveitis, Iritis, Pterygium, Conjunctivitis, Hyposphagma, Trachoma); disorders of choroid (e.g. Chorioretinitis, Choroiditis); Inflammatory Glaucoma; Rosacea; red eye; dry eye disease; Endophthalmitis and/or Panophthalmitis.

A further aspect of the invention pertains a kit, or package, suitable for shipment and storage of the contact lens device prior to its use with a subject. For example, one or more detoxifying contact lens can be provided as a packaged medical device. For example, the contact lens may be stored in essentially any suitable packaging material, container, or other apparatus known in the art, which is capable of maintaining the contact lens devices at appropriate conditions (e.g., sterile conditions, maintained in wet or dry form as specified). In one embodiment, the packaged medical device includes one or more of the contact lens described herein and a packaging container. In one embodiment, the packaging container comprises a contact lens and a solution (saturated or not saturated) of detoxifying agent which is the same as the one present in the soft porous material of the contact lens. In one embodiment, the packaging container comprises an aqueous solution, such as a saline solution or a buffer solution suitable for pH stabilization. In another embodiment, the packaging container is capable of maintaining the contact lens in a dry, lyophilized state. In yet another embodiment, the packaging container is sealed with some humidity or even essentially 100% humidity and capable of maintaining the contact lens in a partially dry state, to minimize alterations of the detoxifying agents present on the soft porous material of the lens device during storage and which may be helpful to decrease the pre-soak time required before application to the eye, to achieve the designed kinetics. In some embodiments, the contact lens device may be packaged in a container and be separated from a solution by a barrier, whereby the barrier may be broken to allow the solution to contact the lens prior to use.

The kits described herein may also contain one or more containers, which can contain components such as the devices and/or active agents as described herein. The kits also may contain instructions for preparing and/or administrating the devices. The kits can also include other containers with one or more solvents, pH stabilizers, surfactants, preservatives, and/or diluents (e.g., normal saline (0.9% NaCl), or 5% dextrose) as well as containers for preparing and/or administering the devices to the subject in need of such treatment.

Additionally, the kit may include containers for other components, for example, solutions to be mixed with the device prior to administration.

Example

The invention proposes a novel approach to the treatment of chronic inflammation of the ocular surface: by continuously removing inflammatory mediators via the adsorption thereof to a specifically designed capture contact lens (FIG. 2), inventors aimed at interrupting the underlying self-sustained vicious cycle. Indeed, it is the common theme of current anti-inflammatory therapy to add exogenous drug molecules to influence internal signalling events of inflammation, with the major drawback of severe side-effects in chronic application. The presented novel taking-up approach dramatically lowers the side-effects; moreover, it can be assumed that important synergies could establish with existing treatments, for instance by lowering the dose of anti-inflammatory drugs necessary for a given treatment goal.

The identification of target patient populations that may benefit from a contact lens of the invention, and the identification of the technical and safety characteristics to be met, dictate material properties of the system, and most importantly the choice of the molecules to be captured: histamine would be a primary candidate in allergy; cytokines such as IL-1, IL-15, IL-6, IL-17 or TNF-α could be targeted in e.g. dry eye disease, but also post-operative chronic inflammation and in chemical or thermal burns. Stromal degradation in severe burns could be further inhibited by capture of matrix degrading enzymes such as N-acetylglucosaminidase, cathepsin D, and MMP-1, MMP-2 and MMP-9. The detox contact lens is also adaptable to well-established mouse models of ocular inflammation such as dry eye disease, allergy or wounding, thus boosting also the research field of ocular inflammation/infection.

In a specific scenario, in terms of capacity, inventors calculated a need to bind through an antibody covalently bound on a contact lens comprising a hydrogel porous material, about 100 ng of an inflammatory mediator, such as for instance a cytokine, if the contact lens is to be worn during daytime (upper cytokine concentration 10 ng/mL; tear flow of 10 microliters per minute, which is 10× above baseline). For most cytokines, this implies immobilization of antibodies, as well as derivatives and/or active fragments thereof, on the soft porous material of the contact lens device. This amount exceeds what can typically be achieved through antibody deposition on the contact lens surface, but can easily be met on the greatly increased surface of the microporous structure of the developed hydrogel (FIG. 3): with 500 ng/cm² of antibody monolayer on a flat surface, an active area of 1 cm², a mass ratio of about 1:5 between cytokine and antibody mass per binding site, and an antibody activity of 25%, one calculates 25 ng of maximal binding capacity; with 5 µm pore size and a porous layer height of 50 µm, one can easily achieve 10 times more binding capacity compared to known solutions.

Without intending to be bound by this theory, the successful exchange of the pore fluid through the blinking cycle also imposes design considerations, namely on the pore size. For instance, an interconnected pore network with an effective pore diameter of 5 µm gives rise a to a Darcy coefficient of some $10^{-12}$ square meters ($r^2/8$) which with a viscosity of $10^{-3}$ Pa*s corresponds to a hydraulic conductivity of $10^{-9}$ m/s/(Pa/m). With a pressure variation of 1 kPa during the blinking cycle, acting on a length scale on the order of 0.5 cm, a flow speed of 0.2 mm/s can therefore be expected, such that fluid evacuation during an interlink interval is feasible as long as flow distances are kept below 1 mm by suitable distribution of the soft porous material.

In a previous phase, before manufacturing of the device of the invention, the capture functionality can be tested by exposing solutions of known concentrations of an inflammatory mediator of interest to the modified gel, and then quantifying adsorption kinetics and equilibrium. This yields the adsorption time constants and affinity constants, and allows to optimize the immobilization and architectural parameters of the capture gel. In another exemplary approach, for what concerns the capture of histamine, the most common inflammatory mediator in allergy-like condition, it is rather more appropriate to use heparan sulfate or other sulphated polyanions bound to or at least partially constituting the gel fibres.

The invention claimed is:

1. An ophthalmic contact lens, comprising:
a porous polymeric material adapted to at least one of take up and neutralize at least one inflammatory mediator present in tear fluid of an eye of a subject wearing the ophthalmic contact lens who has an ophthalmic pathology with an inflammatory component;
wherein the polymeric material
is reversibly compressible,
is configured to allow fluidic exchanges with the tear fluid,
has either an intrinsic affinity for the at least one inflammatory mediator present in the tear fluid or comprises an agent with an affinity for the at least one inflammatory mediator present in the tear fluid,
has a Young's modulus between 100 Pa and 50 kPa, and
has a pore size between about 10 nm and about 300 µm.

2. The ophthalmic contact lens of claim 1, wherein the porous material permits physiologically-driven reversible compression to allow for the fluidic exchanges.

3. The ophthalmic contact lens of claim 1, wherein the fluidic exchanges are obtained via blinking.

4. The ophthalmic contact lens of claim 1, further comprising a detoxifying agent covalently bound to the soft porous polymeric material.

5. The ophthalmic contact lens of claim 1, wherein the porous polymeric material has a thickness between about 1 µm and about 5 mm.

6. The ophthalmic contact lens of claim 1, further comprising an area adapted for vision, wherein the area is positioned at an optical axis of the eye of the subject wearing the ophthalmic contact lens.

7. The ophthalmic contact lens of claim 1, wherein the porous polymeric material is coupled to or assembled on a portion of a surface of the ophthalmic contact lens.

8. The ophthalmic contact lens of claim 4, wherein the detoxifying agent is selected from the group consisting of a protein, an antibody, a derivative of an antibody, a functional fragment, combinations of functional fragments, a growth factor, an enzyme, a transmembrane receptor, a protein receptor, a serum protein, an adhesion molecule, a neurotransmitter, a morphogenetic protein, a matrix protein, a peptide, a polypeptide, a nucleic acid sequence, a hormone, a cytokine, an antigen, a polysaccharide, a lipid molecule, a differentiation factor, a cell, and functional fragments of a cell.

9. The ophthalmic contact lens of claim 1, wherein the at least one inflammatory mediator present in the tear fluid is at least one of an antibody and a histamine.

10. The ophthalmic contact lens of claim 1, further comprising micro-reservoirs fluidically connected with the porous polymeric material.

11. The ophthalmic contact lens of claim 1, wherein the ophthalmic pathology is selected from the group consisting of disorders of an eyelid, disorders of a lacrimal system, disorders of lacrimal orbit, disorders of a sclera, disorders of a cornea, disorders of a conjunctiva, disorders of an iris, disorders of a ciliary body, disorders of a choroid, inflammatory glaucoma, rosacea, red eye, dry eye disease, endophthalmitis, and panophthalmitis.

12. A kit comprising the ophthalmic contact lens of claim 1.

* * * * *